(12) United States Patent
Druma

(10) Patent No.: US 12,239,492 B2
(45) Date of Patent: Mar. 4, 2025

(54) DEVICES, SYSTEMS, AND METHODS FACILITATING ACCESS TO AND MAPPING OF TARGET TISSUE

(71) Applicant: Medtronic Holding Company Sárl, Tolochenaz (CH)

(72) Inventor: Calin Druma, San Jose, CA (US)

(73) Assignee: Medtronic Holding Company Sárl, Tolochenaz (CH)

( * ) Notice: Subject to any disclaimer, the term of this patent is extended or adjusted under 35 U.S.C. 154(b) by 729 days.

(21) Appl. No.: 17/540,994

(22) Filed: Dec. 2, 2021

(65) Prior Publication Data

US 2022/0218434 A1 Jul. 14, 2022

Related U.S. Application Data

(60) Provisional application No. 63/137,465, filed on Jan. 14, 2021.

(51) Int. Cl.
| | | |
|---|---|---|
| *A61B 17/34* | (2006.01) | |
| *A61B 18/00* | (2006.01) | |
| *A61B 90/00* | (2016.01) | |
| *A61B 17/00* | (2006.01) | |

(52) U.S. Cl.
CPC .......... *A61B 90/06* (2016.02); *A61B 17/3423* (2013.01); *A61B 18/00* (2013.01); *A61B 2017/00477* (2013.01); *A61B 2017/3454* (2013.01); *A61B 2018/00577* (2013.01); *A61B 2090/062* (2016.02)

(58) Field of Classification Search
CPC ...... A61B 17/3472; A61B 2017/00477; A61B 2017/3454; A61B 2017/3443; A61B 2017/3423; A61B 2017/347; A61B 18/00; A61B 18/1477; A61B 18/1482; A61B 2018/00023; A61B 2018/00339; A61B 2018/00577; A61B 90/06; A61B 2090/061; A61B 2090/062
See application file for complete search history.

(56) References Cited

U.S. PATENT DOCUMENTS

| | | | |
|---|---|---|---|
| 5,279,570 | A | 1/1994 | Dombrowski et al. |
| 5,665,092 | A | 9/1997 | Mangiardi et al. |
| 5,792,110 | A | 8/1998 | Cunningham |
| 8,128,633 | B2 | 3/2012 | Linderman et al. |

(Continued)

*Primary Examiner* — Michael F Peffley
(74) *Attorney, Agent, or Firm* — Carter, DeLuca & Farrell LLP

(57) ABSTRACT

A surgical access system includes a cannula, a mapping spacer, and a trocar. The cannula includes a proximal base and an elongated cannula body extending distally therefrom. The mapping spacer is configured to releasably engage the proximal base and includes first and second uprights defining a slot therebetween. The trocar includes a proximal handle and an elongated trocar body extending distally therefrom to a distal cutting tip. The elongated trocar body is insertable through the mapping spacer and cannula. In a first orientation of the trocar relative to the mapping spacer, the proximal handle is configured to abut the first and second uprights to inhibit extension of the distal cutting tip from the proximal base beyond an initial position. In a second orientation of the trocar, the proximal handle is slidable through the slot to enable extension of the distal cutting tip distally towards an extended position.

18 Claims, 6 Drawing Sheets

(56) References Cited

U.S. PATENT DOCUMENTS

| | | | |
|---|---|---|---|
| 9,681,889 B1* | 6/2017 | Greenhalgh | A61B 17/3421 |
| 10,123,810 B2* | 11/2018 | Wolters | A61B 17/8805 |
| 10,556,046 B2* | 2/2020 | McGillicuddy | A61M 1/86 |
| 11,246,637 B2* | 2/2022 | Lee | A61B 17/8897 |
| 2003/0199760 A1 | 10/2003 | Curpen et al. | |

* cited by examiner

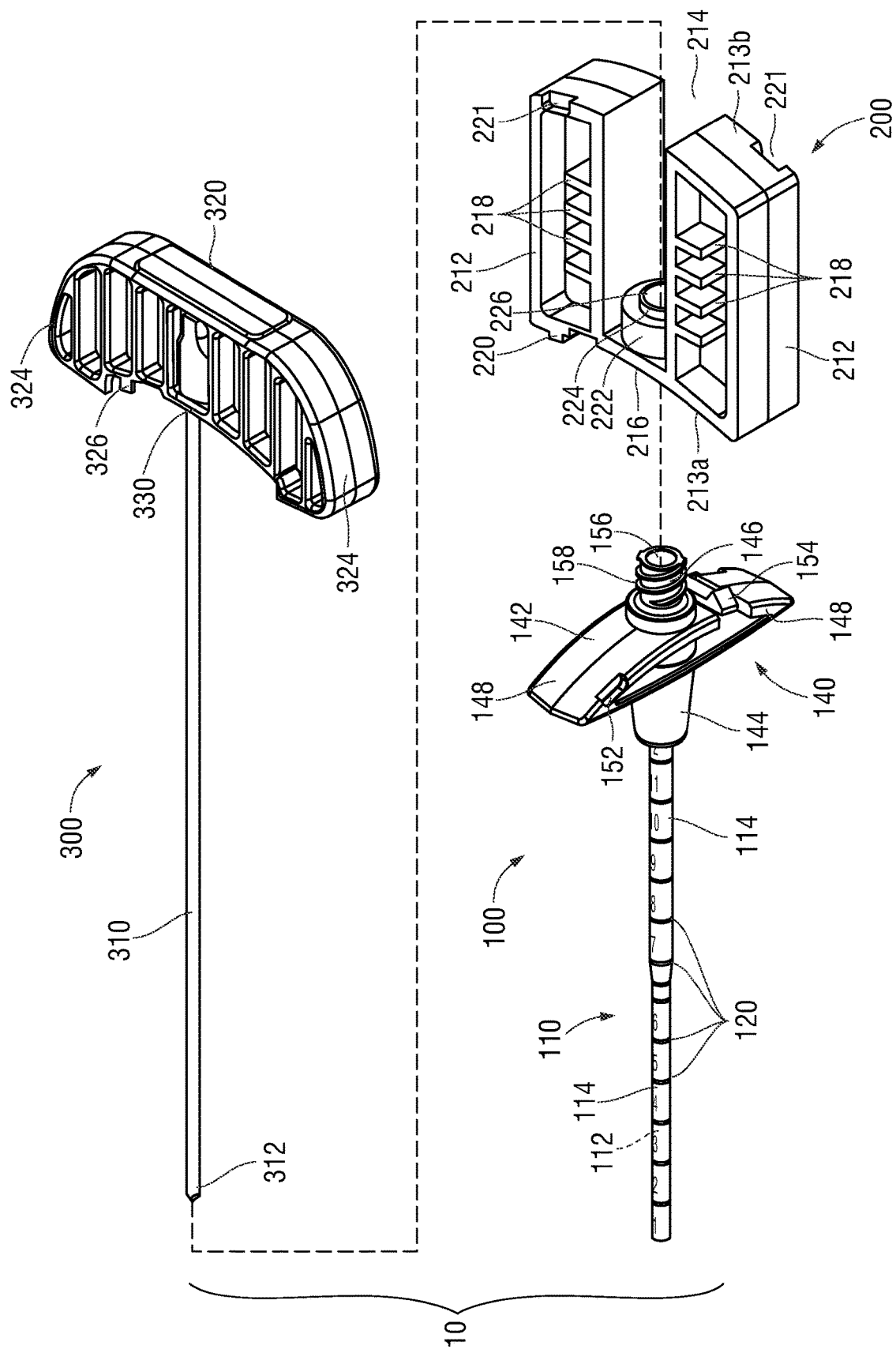

DEVICES, SYSTEMS, AND METHODS FACILITATING ACCESS TO AND MAPPING OF TARGET TISSUE

CROSS-REFERENCE TO RELATED APPLICATIONS

This application claims the benefit of, and priority to, U.S. Provisional Patent Application No. 63/137,465, filed on Jan. 14, 2021, the entire contents of which are hereby incorporated herein by reference.

FIELD

The present disclosure relates generally to tissue access and mapping and, more particularly, to devices, systems, and methods facilitating access to and mapping of target tissue, e.g., a spinal tumor within a vertebra, for performing a surgical task, e.g., ablation, on the target tissue.

BACKGROUND

Treatment of certain diseases requires destruction of malignant tissue growths, e.g., tumors. Tumor tissue can be destroyed via ablation, which involves heating the tumor tissue to sufficiently high temperatures to destroy, e.g., ablate, the tumor tissue while maintaining surrounding healthy tissue at lower temperatures to avoid irreversible damage to the surrounding healthy tissue. Such ablation may be accomplished by applying electromagnetic energy such as RF energy or microwave energy to the tumor tissue to heat and, thereby, ablate the tumor tissue.

Nerve pain and spinal metastases are some of the most common causes of severe pain among patients with cancer. Spinal tumor ablation using electromagnetic radiation can be used for the palliative treatment of painful metastases and nerve pain secondary to advanced cancer disease. Accessing and mapping the spinal tumor prior to performing the ablation facilitates effective ablation of the spinal tumor while inhibiting irreversible damage to the surrounding healthy tissue.

SUMMARY

As used herein, the term "distal" refers to the portion that is being described which is farther from an operator, while the term "proximal" refers to the portion that is being described which is closer to the operator. Terms including "generally," "about," "substantially," and the like, as utilized herein, are meant to encompass variations, e.g., manufacturing tolerances, material tolerances, use and environmental tolerances, measurement variations, and/or other variations, up to and including plus or minus 10 percent. Further, any or all of the aspects described herein, to the extent consistent, may be used in conjunction with any or all of the other aspects described herein.

Provided in accordance with aspects of the present disclosure is a surgical access system including a cannula, a mapping spacer, and a trocar. The cannula includes a proximal base and an elongated cannula body extending distally from the proximal base. The mapping spacer is configured to releasably engage the proximal base of the cannula and includes first and second uprights defining a slot therebetween. The trocar includes a proximal handle and an elongated trocar body extending distally from the proximal handle to a distal cutting tip. The elongated trocar body is configured for insertion through the mapping spacer and the cannula such that the distal cutting tip extends distally from the elongated cannula body. In a first orientation of the trocar relative to the mapping spacer, the proximal handle is configured to abut the first and second uprights to inhibit extension of the distal cutting tip from the proximal base beyond an initial position. In a second orientation of the trocar relative to the mapping spacer, the proximal handle is configured to slide through the slot of the mapping spacer to enable extension of the distal cutting tip distally from the initial position towards an extended position.

In an aspect of the present disclosure, the mapping spacer includes markings disposed on at least one of the first or second uprights to enable determination of a depth of extension of the distal cutting tip from the initial position towards the extended position. In such aspects, the proximal handle of the trocar may include a reference point for comparison with the markings to enable determination of the depth of extension.

In another aspect of the present disclosure, the trocar is rotatable 90 degrees relative to the mapping spacer to transition between the first and second orientations.

In still another aspect of the present disclosure, the proximal handle includes first and second shoulders extending outwardly therefrom. In the first orientation of the trocar, the first and second shoulders are substantially aligned with the first and second uprights, respectively. In the second orientation, the first and second shoulders are substantially perpendicular relative to the first and second uprights.

In yet another aspect of the present disclosure, the proximal base of the cannula defines a coupler configured to releasably engage a coupler of the mapping spacer. The couplers, in aspects, may define complementary threading to enable threaded engagement of the mapping spacer with the proximal base of the cannula.

In still yet another aspect of the present disclosure, the proximal base of the cannula and a distal face of the mapping spacer include at least one of complementary alignment features or complementary engagement features to enable alignment or engagement, respectively, of the proximal base of the cannula and the mapping spacer with one another.

In another aspect of the present disclosure, a proximal face of the mapping spacer and the proximal handle of the trocar include at least one of complementary alignment features or complementary engagement features to enable alignment or engagement, respectively, of the mapping spacer and the proximal handle of the trocar in the first orientation of the trocar.

In another aspect of the present disclosure, the access system further includes an ablation device including an ablation probe configured for insertion through the elongated cannula body in the absence of the elongated trocar body.

In yet another aspect of the present disclosure, the elongated cannula body includes markings disposed thereon to enable determination of insertion thereof. Additionally or alternatively, the elongated cannula body includes a proximal section defining a first diameter, a distal section defining a second, smaller diameter, and a transition section extending between and interconnecting the proximal and distal sections.

A method of surgery in accordance with aspects of the present disclosure includes engaging a mapping spacer with a proximal base of a cannula, wherein the cannula includes an elongated cannula body extending distally from the proximal base. The method further includes inserting a trocar, in a first orientation, through the mapping spacer and the cannula until a proximal handle of the trocar abuts the mapping spacer to define an initial position wherein a distal cutting tip of the trocar extends distally an initial distance from the elongated cannula body. The method additionally includes advancing the cannula, the mapping spacer, and the trocar together with one another such that the distal cutting tip of the trocar is advanced distally through tissue. The proximal handle of the trocar is rotated from the first orientation to a second orientation such that the proximal handle is aligned with a slot defined through the mapping spacer. Thereafter, the trocar is advanced distally relative to the cannula and the mapping spacer such that the proximal handle slides distally through the slot of the mapping spacer and such that the distal cutting tip is advanced further distally through tissue from the initial position towards an extended position.

In an aspect of the present disclosure, the method further includes determining a distance the distal cutting tip is advanced from the initial position towards the extended position using markings on the mapping spacer.

In another aspect of the present disclosure, advancing the cannula, the mapping spacer, and the trocar together with one another includes advancing the distal cutting tip of the trocar to a proximal side of target tissue. Advancing the trocar distally relative to the cannula and the mapping spacer, in such aspects, may include advancing the distal cutting tip of the trocar through the target tissue to a distal side of the target tissue. A dimension of the target tissue may thus be determined using markings on the mapping spacer.

In still another aspect of the present disclosure, the method further includes withdrawing the trocar, disengaging the mapping spacer from the proximal base of the cannula, inserting an ablation probe through the cannula such that a distal portion of the ablation probe extends distally from the elongated cannula body into target tissue, and energizing the ablation probe to ablate the target tissue.

BRIEF DESCRIPTION OF DRAWINGS

The above and other aspects and features of the present disclosure will become more apparent in view of the following detailed description when taken in conjunction with the accompanying drawings wherein like reference numerals identify similar or identical elements.

FIG. 2 is an exploded, perspective view of the access system of FIG. 1A;

DETAILED DESCRIPTION

Figure 1A:
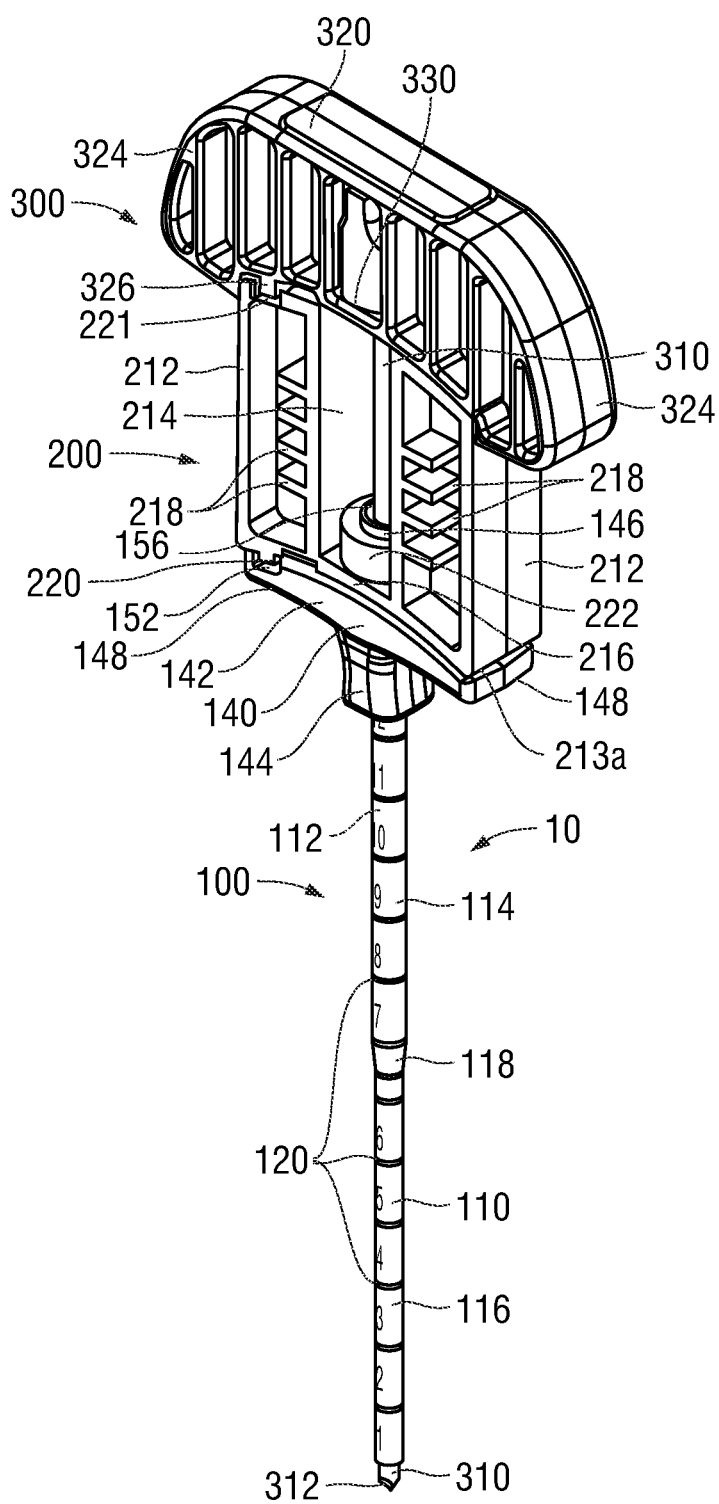
FIG. 1A is a perspective view of an access system provided in accordance with the present disclosure including a cannula, a mapping spacer, and a trocar, wherein the access system is disposed in an insertion configuration.
Figure 1B:
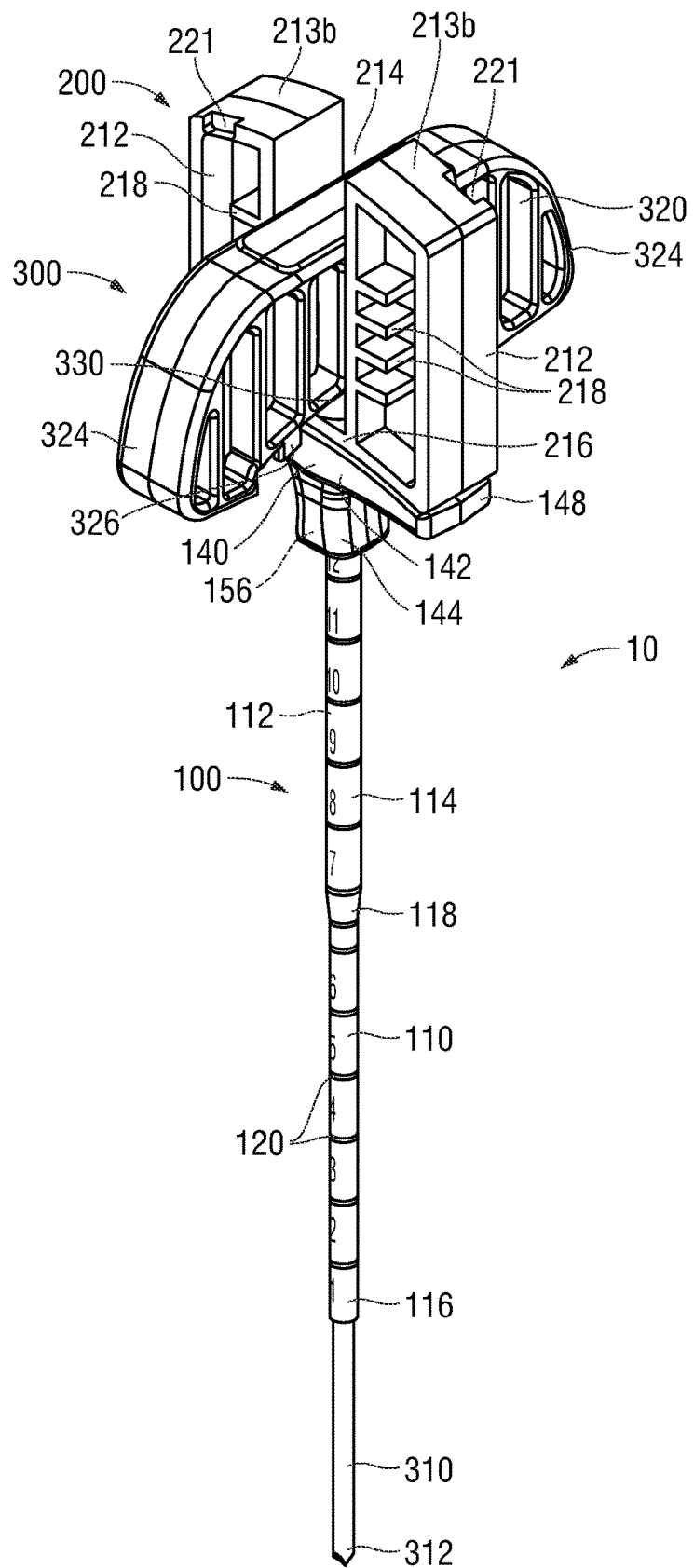
FIG. 1B is a perspective view of the access system of FIG. 1A, wherein the access system is disposed in a mapping configuration.

FIGS. 1A, 1B, and 2 illustrate an access system in accordance with the present disclosure shown generally identified by reference numeral 10. Access system 10 may be utilized to facilitate access to and mapping of, for example, a spinal tumor within a vertebra to facilitate spinal tumor ablation, as detailed below, or may be utilized to facilitate access to and/or mapping of other tissue structures, tissue at other anatomical locations, and/or for otherwise treating tissue. Access system 10 generally includes a cannula 100, a mapping spacer 200, and an insertion device such as a trocar 300.

Cannula 100 of access system 10 includes an elongated tubular body 110 and a proximal base 140. Elongated cannula body 110 defines a lumen 112 extending longitudinally therethrough. Elongated cannula body 110 may define a substantially constant diameter along its length, may include two or more sections of different diameter, and/or may include one or more tapered sections. For example, elongated cannula body 110 may include a proximal section 114 of a first diameter and a distal section 116 of a second, smaller diameter. A transition section 118 may be disposed between and interconnect the proximal and distal sections 114, 116 to define a smooth transition between the proximal and distal sections 114, 116. Other configurations are also contemplated. In aspects, elongated cannula body 110 defines a plurality of depth markers 120 (each including a demarcation line and a reference indicium, for example) spaced-apart along at least a portion of the length of elongated cannula body 110. Depth markers 120 may be configured to facilitate visual, echogenic, radiogenic, fluorogenic, and/or other suitable identification of an insertion depth of elongated cannula body 110 into a patient and/or an anatomical structure within the patient.

Proximal base 140 of cannula 100 includes a base body 142, a neck 144 extending distally from base body 142, and a coupler 146 extending proximally from base body 142. Base body 142 is configured to facilitate grasping and manipulation by an operator, and defines a pair of outwardly-extending shoulders 148. One or both of shoulders 148 may include an alignment feature 152, e.g., a recess, and/or an engagement feature 154, e.g., a cantilever engagement arm. Neck 144, as noted above, extends distally from base body 142 and supports a proximal end portion of elongated cannula body 110, e.g., therein, thereon, or otherwise attached thereto. Coupler 146 extends proximally from base body 142 and cooperates with base body 142 and neck 144 to define a lumen 156 extending longitudinally through proximal base 140. Lumen 156 is disposed coaxially and in communication with lumen 112 of elongated cannula body 110. Coupler 146 includes threading 158 or other suitable engagement feature(s) on an exterior surface thereof or otherwise positioned.

Continuing with reference to FIGS. 1A-2, mapping spacer 200 of access system 10 may be formed as a single, monolithic component, e.g., via injection molding, 3D printing, etc., or may be formed via attachments of plural components. Mapping spacer 200 defines a generally U-shaped configuration and having a pair of spaced-apart uprights 212 separated by a slot 214 and interconnected at distal ends thereof via a distal backspan 216. Either or both uprights 212 includes a plurality of depth markers 218 spaced-apart along at least a portion of the length of mapping spacer 200. Depth markers 218 may be embossed on either or both sides of either or both uprights 212, e.g., during formation of mapping spacer 200, or may be adhered, printed, or otherwise attached on either or both sides of either or both uprights 212. Depth markers 218, as detailed below, are configured to facilitate visual identification of a depth of advancement of an insertion device, e.g., trocar 300, from elongated cannula body 110 of cannula 100. One or both of uprights 212 may additionally include an alignment feature 220, e.g., a tab, and/or an engagement feature (not shown), e.g., a catch, on a distal face 213a thereof. Alternatively or additionally, one or both of uprights 212 may include an alignment feature 221, e.g., a recess, a proximal face 213b thereof.

Distal backspan 216 of mapping spacer 200 includes a coupler 222 defining a lumen 224 extending longitudinally therethrough. Coupler 222 includes threads 226 or other suitable engagement feature(s) on an interior surface thereof surrounding lumen 224 or otherwise positioned. Threading 226 of coupler 222 of mapping spacer 200 is complementary to threading 158 of coupler 146 of cannula 100 to enable threaded engagement of coupler 222 about coupler 146, although other suitable complementary engagements are also contemplated. Upon sufficient threaded engagement of coupler 222 of mapping spacer 200 about coupler 146 of cannula 100, the alignment feature 220 of mapping spacer 200 is engaged with the alignment feature 142 of cannula 100, e.g., the tab is received within the recess, and the engagement feature 154 of cannula 100 is engaged with the engagement feature (not shown) of mapping spacer 200, e.g., the cantilever engagement arm is snap-fit into engagement within the catch. In this manner, mapping spacer 200 is secured to cannula 100 in fixed orientation relative thereto. In this engaged condition, lumen 224 of mapping spacer 200, lumen 156 of proximal base 140 of cannula 100, and lumen 112 of elongated cannula body 110 of cannula 100 are coaxially disposed and in communication with one another to permit insertion an insertion device, e.g., trocar 300, therethrough.

Referring still to FIGS. 1A-2, trocar 300 of access system 10 includes an elongated trocar body 310 and a proximal handle 320 supporting elongated trocar body 310 at a proximal end of elongated trocar body 310. Elongated trocar body 310 defines a suitable diameter and length to enable insertion of elongated trocar body 310 through mapping spacer 200 and cannula 100 and into an internal surgical site. Elongated trocar body 310 may include a distal cutting tip 312 configured to penetrate tissue including hard tissue such as bone. Distal cutting tip 312 may define one or more cutting points, cutting edges, and/or other suitable cutting features to facilitate penetrating, e.g., malleting, tissue to define an access pathway to an internal surgical site, e.g., a spinal tumor within a vertebra. Elongated trocar body 310 may be rigid, semi-rigid, malleable, resiliently flexible, or otherwise configured and may define a linear configuration or a pre-bent configuration. Elongated cannula body 110 of cannula 100 may, similarly or differently, be rigid, semi-rigid, malleable, resiliently flexible, or otherwise configured and may define a linear configuration or a pre-bent configuration. In this manner, elongated cannula body 110 of cannula 100 and elongated trocar body 310 of trocar 300 may be configured to enable use of access system 10 to facilitate access to any anatomical location from any directional approach.

Proximal handle 320 of trocar 300 supports the proximal end of elongated trocar body 310 and includes a pair of outwardly-extending shoulders 324. Shoulders 324 facilitate grasping and manipulation of proximal handle 320. One or both of shoulders 324 may further include an alignment feature 326 (and/or an engagement feature), e.g., a tab, extending therefrom. In aspects, shoulder 324 includes an alignment feature 326 (and/or an engagement feature) on a front side of proximal handle 320 while the other shoulder 324 includes an alignment feature 326 (and/or an engagement feature) on an opposite, rear side of proximal handle 320. In such aspects, mapping spacer 200 may be configured with an alignment feature 221 (and/or an engagement feature), e.g., a tab, on the proximal face 213b of one of the uprights 212 on a front side thereof and another alignment feature 221 (and/or an engagement feature), e.g., a tab, on the proximal face 213b of the other upright 212 on a rear side thereof. In this manner, with shoulders 324 of proximal handle 320 of trocar 300 substantially aligned with uprights 212 of mapping spacer 200, elongated trocar body 310 of trocar 300 may be inserted through mapping spacer 200 and cannula 100 until proximal handle 320 abuts proximal face 213b of mapping spacer 200, whereby alignment features 221 are received within alignment features 326 to rotationally fix and, in some aspects, engage (via engagement features), proximal handle 320 of trocar 300 and mapping spacer 200 with one another (see FIG. 1A).

Referring in particular to FIG. 1A, with mapping spacer 200 engaged with cannula 100 as detailed above, and trocar 300 abutting (and, in aspects, engaged with) mapping spacer 200 in the aligned orientation of shoulders 324 of proximal handle 320 relative to uprights 212 of mapping spacer 200, access system 10 defines an insertion configuration wherein distal cutting tip 312 of elongated trocar body 310 of trocar 300 is disposed in an initial position extending a relatively minimal distance from the distal end of elongated cannula body 110 of cannula 100 and is inhibited from further extension therefrom via the abutment (and engagement, in aspects) of proximal handle 320 of trocar 300 with uprights 212 of mapping spacer 200. In this insertion configuration, access system 10 may be utilized to penetrate tissue to a position wherein distal cutting tip 312 of elongated trocar body 310 is positioned proximally adjacent target tissue, e.g., a spinal tumor to be ablated, as detailed below. In this manner, an access pathway to the target tissue is created.

With additional reference to FIG. 1B, in order to permit advancement of elongated trocar body 310 relative to cannula 110 and mapping spacer 200, e.g., to enable mapping of target tissue, proximal handle 320 of trocar 300 is rotated 90 degrees relative to mapping spacer 200 such that shoulders 324 of proximal handle 320 of trocar 300 are oriented substantially perpendicularly relative to uprights 212 of mapping spacer 200 and in alignment with the open sides of slot 214 of mapping spacer 200. As can be appreciated, alignment features 221, 326 (and any engagement features of trocar 300 and mapping spacer 200) are disengaged from one another upon such rotation of trocar 300. With proximal handle 320 disposed substantially perpendicular relative to mapping spacer 200 and in substantial alignment with the open sides of slot 214 of mapping spacer 200, access system 10 defines a mapping configuration wherein distal cutting tip 312 of elongated trocar body 310 may be advanced distally into the target tissue and relative to mapping spacer 200 and cannula 100. That is, proximal handle 320 of trocar 300 may be advanced distally through slot 214 of mapping spacer 200 to extend distal cutting tip 312 of elongated trocar body 310 of trocar 300 from the initial position further distally relative to the distal end of elongated cannula body 110 of cannula 100 to an extended position, e.g., through the target tissue to the distal side of the target tissue. The distance distal cutting tip 312 is advanced from the initial position to the extended position and, thus, the diameter or other dimension through the target tissue, is determined by comparing the position of a reference point 330 of proximal handle 320 to depth markers 218 of uprights 212 of mapping spacer 200. Depth markers 218 may be disposed at consistent intervals, include indicia, and/or may otherwise be configured to readily enable determination of the extension distance of distal cutting tip 312. Reference point 330 of proximal handle 320 may be a distal face of proximal handle 320 (see FIG. 2) or any other suitable structural feature of or marking on proximal handle 320.

Figure 3:
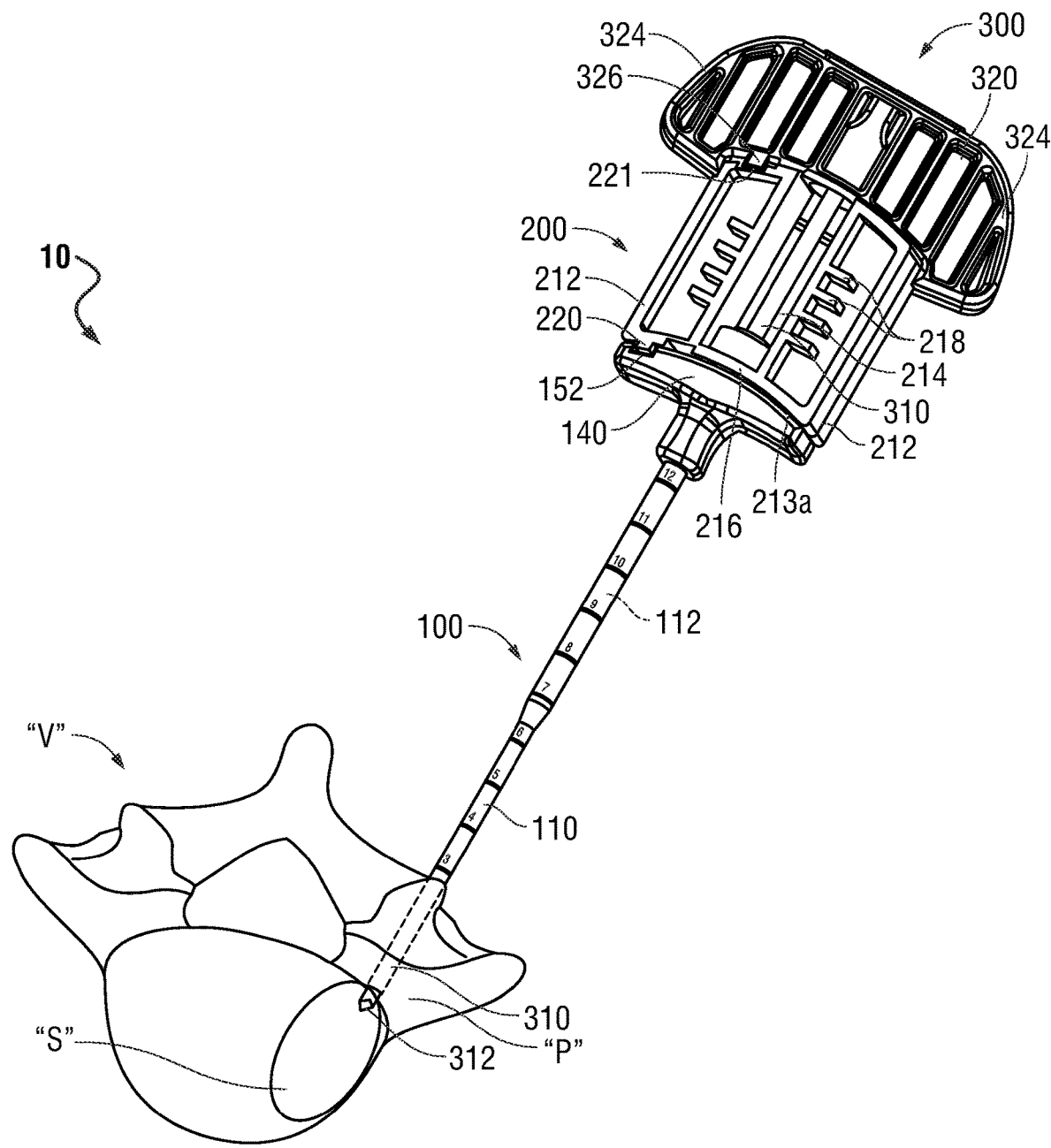
FIG. 3 is a perspective view of the access system of FIG. 1A disposed in the insertion configuration and extending into a vertebra with the trocar disposed at a proximal side of a spinal tumor to be ablated.
Figure 4:
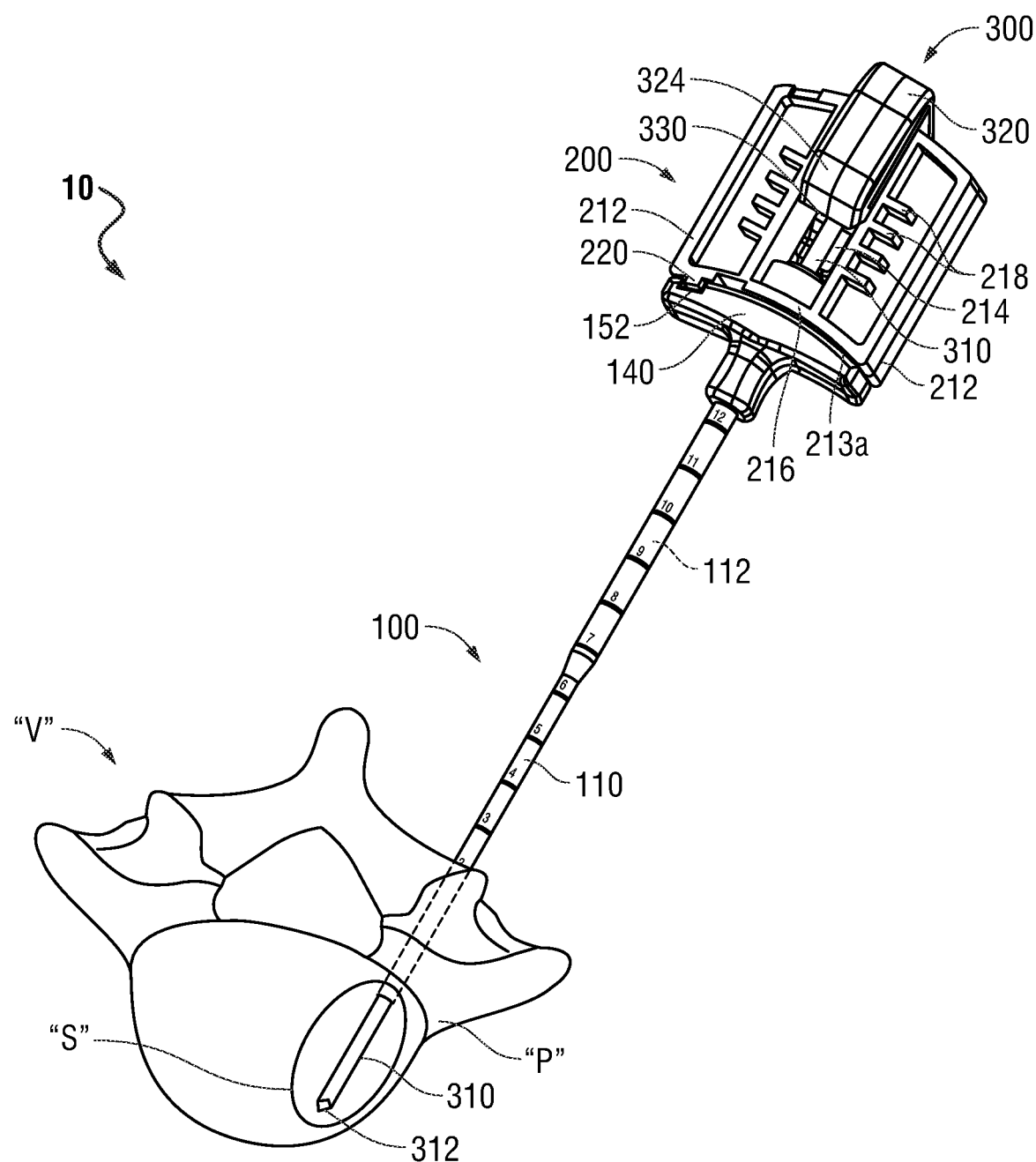
FIG. 4 is a perspective view of the access system of FIG. 1A disposed in the mapping configuration and extending into a vertebra with the trocar disposed through the spinal tumor to a distal side thereof.

Turning to FIGS. 3-4, in conjunction with FIG. 2, the use of access system 10 to access and map a spinal tumor "S" within a vertebra "V" is detailed. Initially, with access system 10 disposed in the insertion configuration, access system 10, led by distal cutting tip 312 of elongated trocar body 310 of trocar 300, is advanced, e.g., through a skin incision, to a position adjacent a pedicle "P" of the vertebra "V." Thereafter, access system 10 is advanced further distally whereby distal cutting tip 312 is malleted through the vertebra "V" to a position adjacent a proximal side of the spinal tumor "S." Once this position, shown in FIG. 3, is achieved, an access pathway to the spinal tumor "S" is established.

With distal cutting tip 312 malleted through the vertebra "V" into position adjacent the proximal side of the spinal tumor "S," proximal handle 320 is rotated 90 degrees to transition access system 10 from the insertion configuration to the mapping configuration and, thereafter, proximal handle 320 is advanced distally through slot 214 of mapping spacer 200 to advance distal cutting tip 312 through the spinal tumor "S" to the distal side thereof. Reference point 330 of proximal handle 320 is compared to the appropriate depth marker 218 of mapping spacer 200 to enable determination of the extension distance of distal cutting tip 312 and, thus, the distance across the spinal tumor "S" from the proximal side thereof to the distal side thereof. The above access and mapping may be performed with the aid of fluoroscopy, ultrasound, endoscopy, or other suitable guidance. As can be appreciated, access system 10 enables the above-detailed access and mapping without requiring additional tools and/or tool exchange.

Figure 5:
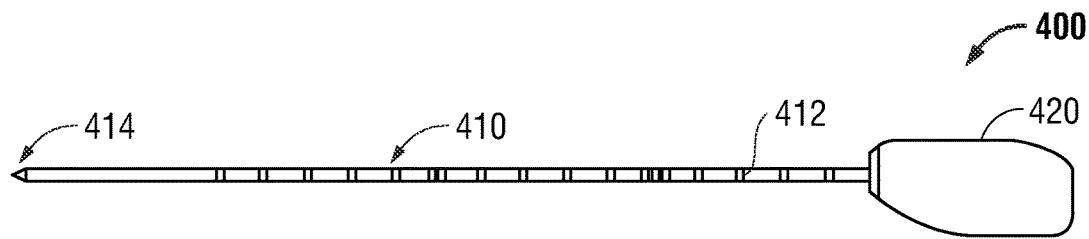
FIG. 5 is a side view of an ablation device configured for use with the access system of FIG. 1A.
Figure 6:
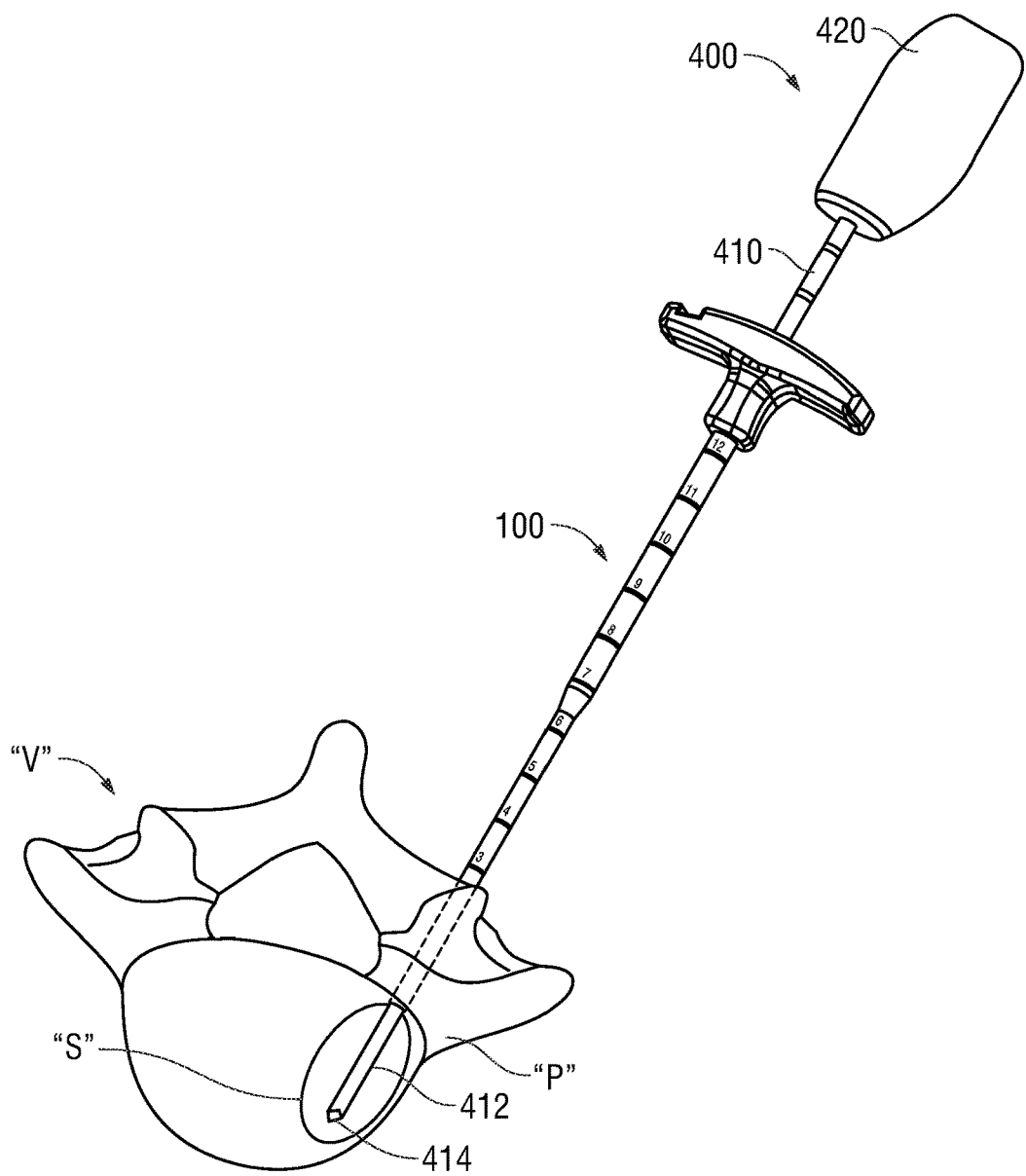
FIG. 6 is a perspective view of the ablation device of FIG. 5 inserted through the cannula of the access system of FIG. 1A, into the vertebra, and into the spinal tumor for ablating the spinal tumor.

Referring also to FIGS. 5 and 6, in conjunction with FIG. 2, with an access pathway to the spinal tumor "S" establish and with the spinal tumor "S" mapped, trocar 300 may be withdrawn from cannula 100 and mapping spacer 200 and mapping spacer 200 may be disengaged and removed from cannula 100, leaving cannula 100 in position. Based on the results of the mapping of the spinal tumor "S," a suitable ablation probe may be selected to enable appropriate access to and effective ablation of the spinal tumor "S" while inhibiting irreversible damage to the surrounding healthy tissue. This selection may be based on, for example, a length, diameter, ablation zone volume, operational temperature(s), shape (e.g., curvature or linearity), energy modality (e.g., bipolar RF, monopolar RF, microwave, etc.), features (e.g., fluid cooled), and/or other aspects of the ablation probe.

An exemplary ablation device 400 is illustrated in FIG. 5 generally including an ablation probe 410 and a connection hub 420. Ablation probe 410 defines an elongated configuration and may be substantially linear, curved, or otherwise configured to facilitate accessing tissue to be ablated. In aspects, ablation probe 410 is at least partially formed form a resiliently flexible material, e.g., a shape memory material, to enable resilient flexion of ablation probe 410 to assume a desired trajectory for accessing tissue to be ablated. In additional or alternative aspects, ablation probe 410 is at least partially formed from a rigid, semi-rigid, malleable, and/or other suitable material(s). Ablation probe 410 includes a body 412 and a distal tip 414. Distal tip 414 may be configured to facilitate penetration into and/or anchoring within tissue including hard tissue, e.g., bone. A portion of body 412 and/or distal tip 414 cooperate to define an operative portion of ablation probe 410 configured to deliver energy, e.g., bipolar RF, monopolar RF, microwave, etc., to tissue to heat and thereby ablate tissue.

Connection hub 420 supports a proximal end portion of body 412 of ablation probe 410 with ablation probe 410 extending distally from connection hub 420 to distal tip 414. Connection hub 420 may function as a handle of ablation device 400, enabling a user to grasp and manipulate connection hub 420 to thereby manipulate ablation probe 410. Electrical connections such as, for example, electrode lead wires, e.g., an active electrode lead (in monopolar RF configurations) or positive and negative electrode leads (in bipolar RF configurations), sensing leads, e.g., for temperature sensors, thermocouple leads, and/or other energy-delivery, sensing, or communication leads extend from a cable (not shown) into connection hub 420 for connection to and/or routing through ablation probe 410. Inflow and outflow tubing (not shown) may likewise extend into connection hub 420 for routing to and/or through ablation probe 410, e.g., in configurations wherein cooling fluid is circulated through ablation probe 410 to cool ablation probe 410. The cable (not shown) of ablation device 400 is configured to connect to an energy source (not shown), e.g., an electrosurgical generator, for powering and controlling ablation probe 410.

Once the access pathway to the spinal tumor "S" is established, the spinal tumor "S" mapped, and trocar 300 and mapping spacer 200 removed, as noted above, ablation probe 410 of ablation device 400 is inserted through cannula 100 and, based upon the mapping of the spinal tumor "S," is extended into the spinal tumor "S" to a suitable position for ablating the spinal tumor "S" (or initially ablating the spinal tumor "S," in situations where multiple positions of ablation probe 410 and multiple ablations are required). Once positioned appropriately, ablation probe 410 may be energized to ablate the spinal tumor "S" while inhibiting damage to healthy surrounding tissue. Once the spinal tumor "S" is sufficiently ablated, ablation probe 410 and cannula 100 are removed from the patient.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques).

While several configurations of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular configurations. Those skilled in the art will envision other modifications within the scope and spirit of the claims appended hereto.

What is claimed is:

1. A surgical access system, comprising:
   a cannula including a proximal base and an elongated cannula body extending distally from the proximal base;

a mapping spacer configured to releasably engage the proximal base of the cannula, the mapping spacer including first and second uprights defining a slot therebetween; and a trocar including a proximal handle and an elongated trocar body extending distally from the proximal handle to a distal cutting tip, the elongated trocar body configured for insertion through the mapping spacer and the cannula such that the distal cutting tip extends distally from the elongated cannula body, wherein, in a first orientation of the trocar relative to the mapping spacer, the proximal handle is configured to abut the first and second uprights to inhibit extension of the distal cutting tip from the proximal base beyond an initial position, and wherein, in a second orientation of the trocar relative to the mapping spacer, the proximal handle is configured to slide through the slot of the mapping spacer to enable extension of the distal cutting tip distally from the initial position towards an extended position.

2. The surgical access system according to claim 1, wherein the mapping spacer includes markings disposed on at least one of the first or second uprights to enable determination of a depth of extension of the distal cutting tip from the initial position towards the extended position.

3. The surgical access system according to claim 2, wherein the proximal handle of the trocar includes a reference point for comparison with the markings to enable determination of the depth of extension.

4. The surgical access system according to claim 1, wherein the trocar is rotatable 90 degrees relative to the mapping spacer to transition between the first and second orientations.

5. The surgical access system according to claim 1, wherein the proximal handle includes first and second shoulders extending outwardly therefrom, wherein, in the first orientation of the trocar, the first and second shoulders are substantially aligned with the first and second uprights, respectively, and wherein, in the second orientation, the first and second shoulders are substantially perpendicular relative to the first and second uprights.

6. The surgical access system according to claim 1, wherein the proximal base of the cannula defines a coupler configured to releasably engage a coupler of the mapping spacer.

7. The surgical access system according to claim 6, wherein the couplers define complementary threading to enable threaded engagement of the mapping spacer with the proximal base of the cannula.

8. The surgical access system according to claim 1, wherein the proximal base of the cannula and a distal face of the mapping spacer include at least one of complementary alignment features or complementary engagement features to enable alignment or engagement, respectively, of the proximal base of the cannula and the mapping spacer with one another.

9. The surgical access system according to claim 1, wherein a proximal face of the mapping spacer and the proximal handle of the trocar include at least one of complementary alignment features or complementary engagement features to enable alignment or engagement, respectively, of the mapping spacer and the proximal handle of the trocar in the first orientation of the trocar.

10. The surgical access system according to claim 1, further comprising an ablation device including an ablation probe configured for insertion through the elongated cannula body in the absence of the elongated trocar body.

11. The surgical access system according to claim 1, wherein the elongated cannula body includes markings disposed thereon to enable determination of insertion thereof.

12. The surgical access system according to claim 1, wherein the elongated cannula body includes a proximal section defining a first diameter, a distal section defining a second, smaller diameter, and a transition section extending between and interconnecting the proximal and distal sections.

13. A method of surgery, comprising:
engaging a mapping spacer with a proximal base of a cannula, the cannula including an elongated cannula body extending distally from the proximal base;
inserting a trocar, in a first orientation, through the mapping spacer and the cannula until a proximal handle of the trocar abuts the mapping spacer to define an initial position wherein a distal cutting tip of the trocar extends distally an initial distance from the elongated cannula body;
advancing the cannula, the mapping spacer, and the trocar together with one another such that the distal cutting tip of the trocar is advanced distally through tissue;
rotating the proximal handle of the trocar from the first orientation to a second orientation such that the proximal handle is aligned with a slot defined through the mapping spacer; and
advancing the trocar distally relative to the cannula and the mapping spacer such that the proximal handle slides distally through the slot of the mapping spacer and such that the distal cutting tip is advanced further distally through tissue from the initial position towards an extended position.

14. The method according to claim 13, further comprising determining a distance the distal cutting tip is advanced from the initial position towards the extended position using markings on the mapping spacer.

15. The method according to claim 13, wherein advancing the cannula, the mapping spacer, and the trocar together with one another includes advancing the distal cutting tip of the trocar to a proximal side of target tissue.

16. The method according to claim 15, wherein advancing the trocar distally relative to the cannula and the mapping spacer includes advancing the distal cutting tip of the trocar through the target tissue to a distal side of the target tissue.

17. The method according to claim 16, further comprising determining a dimension of the target tissue using markings on the mapping spacer.

18. The method according to claim 13, further comprising:
withdrawing the trocar;
disengaging the mapping spacer from the proximal base of the cannula;
inserting an ablation probe through the cannula such that a distal portion of the ablation probe extends distally from the elongated cannula body into target tissue; and
energizing the ablation probe to ablate the target tissue.

* * * * *